United States Patent [19]

Lee et al.

[11] 3,996,259

[45] Dec. 7, 1976

[54] OXIDATION OF ORGANIC COMPOUNDS BY AQUEOUS HYPOHALITES USING PHASE TRANSFER CATALYSIS

[75] Inventors: George A. Lee, Wayland; Harold H. Freedman, Newton Center, both of Mass.

[73] Assignee: The Dow Chemical Company, Midland, Mich.

[22] Filed: Nov. 6, 1975

[21] Appl. No.: 629,338

[52] U.S. Cl. .................... 260/465 B; 260/348 C; 260/348 R; 260/413; 260/465 R; 260/465.1; 260/465.2; 260/530 R; 260/566 D; 260/586 P; 260/591; 260/593 R; 260/603 C
[51] Int. Cl.$^2$ ................ C07C 47/54; C07C 49/76; C07C 120/00; C07C 120/10
[58] Field of Search .......... 260/465 B, 465 R, 599, 260/530 R, 465.1, 465.2, 593 R, 603 C, 591, 566 D

[56] References Cited
OTHER PUBLICATIONS

Starks, J. Amer. Chem. Soc., vol. 93, 195–199 (1971).
Starks et al., Chemical Abstracts, vol. 72, 115271t (1970).

*Primary Examiner*—Lewis Gotts
*Assistant Examiner*—Dolph H. Torrence
*Attorney, Agent, or Firm*—G. R Plotecher; L. W. White

[57] ABSTRACT

Organic compounds oxidizable by hypohalite ion, such as amines, amides, primary and secondary alcohols, and alkanals are efficiently oxidized in a biphasic mixture comprising:

a. a water immiscible, liquid organic phase comprising an organic compound oxidizable by hypohalite ion; with b. an aqueous phase containing hypohalite ion; and c. a catalytic amount of a quaternary ammonium salt and/or a quaternary phosphonium salt.

13 Claims, No Drawings

OXIDATION OF ORGANIC COMPOUNDS BY AQUEOUS HYPOHALITES USING PHASE TRANSFER CATALYSIS

BACKGROUND OF THE INVENTION

1. Field of the Invention

This invention relates to the oxidation of organic compounds by aqueous hypohalites. More particularly, this invention relates to the oxidation of organic compounds oxidizable by hypohalite ion in a biphasic mixture using phase transfer catalysis.

2. Description of the Prior Art

Various methods are known for oxidizing organic compounds by hypohalite ion. For example, C. Y. Meyers, J. Org. Chem., 26, 1046 (1961), teaches the preparation of benzaldehyde by reacting benzyl alcohol with aqueous, methanolic inorganic hypochlorite. E. S. Wallis and J. F. Lane, Org. Reactions, 3, 267 (1947), teach the Hoffman rearrangement of amides to amines by reacting alkali metal hypohalite and a primary amide in aqueous caustic.

Oxidations catalyzed by quaternary onium salts have been reported by C. M. Starks, J. Amer. Chem. Soc., 93, 195 (1971). There, nonanoic acid as prepared in 91 percent yield by reacting aqueous potassium permanganate with 1-decene in the presence of tricaprylmethylammonium chloride. However, no such catalyzed reaction has been reported where hypohalite ion was the oxidizing agent.

SUMMARY OF THE INVENTION

A novel process for oxidizing organic compounds oxidizable by hypohalite ion in a biphasic mixture using phase transfer catalysis has been discovered. The process comprises reacting by contacting:

a. a water-immiscible, liquid organic phase comprising an organic compound oxidizable by hypohalite ion; with b. an aqueous phase containing hypohalite ion; and c. a catalytic amount of a quaternary ammonium salt and/or a quaternary phosphonium salt. The novel process proceeds under mild conditions in high yields and in reduced reaction time. In every case, the phase transfer catalyzed hypohalite oxidations are more efficient than the noncatalyzed hypohalite oxidations. Moreover, said catalyzed hypohalite oxidations are highly selective. For example, a secondary alcohol is quantitatively oxidized by this invention to a ketone before the ketone itself is oxidized via the haloform reaction to a carboxylic acid.

DETAILED DESCRIPTION OF THE INVENTION

Any organic compound oxidizable by aqueous hypohalite ion can be oxidized by this invention. Illustrative of these compounds are amines, amides, alkanals, primary and secondary alkanols, and organic compounds containing an activated double bond, i.e. an organic compound containing the structure

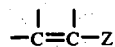

wherein Z is an electron withdrawing group, such as carbonyl, nitrile, ester, etc. Typical oxidation reactions include amines to N-haloimines or nitriles, amides to N-haloimines or nitriles, alkanals to carboxylic acids, primary alkanols to alkanals, secondary alkanols to ketones, and enones to epoxies, i.e., 2-cyclohexenone to 2-cyclohexenone oxide.

The hypohalites here used are hypochlorite, hypobromite, hypoiodite, or any combination thereof. Any suitable source of hypohalite ion can be used in the practice of this invention, but typically the alkali metal hypohalites are used. Due to reasons of familiarity and general availability, hypochlorite is preferred over the other hypohalites.

The catalysts here used are quaternary ammonium and phosphonium salts and are known in the art as phase transfer catalysts. The salts are described by Starks and Napier in British patent 1,227,144 and by Starks in the J. Amer. Chem. Soc., 93, 195 (1971). Suitable onium salts have a minimum solubility of at least about 1 weight percent in both the organic phase and the aqueous phase at 25° C. The ammonium salts are preferred over the phosphonium salts and benzyltrimethyl-, benzyltriethyl-, and tetra-n-butylammonium chlorides and bromides are most preferred.

To further illustrate the type of ammonium salt which can be used, suitable ammonium salts are represented by the formula $R_1R_2R_3R_4N^+A^-$ wherein $R_1$–$R_4$ are hydrocarbyl groups, i.e. alkyl, aryl, alkylaryl, arylalkyl, cycloalkyl, etc., and $R_1$ can join with $R_2$, or $R_2$ with $R_3$, etc. to form a 5- or 6-membered heterocyclic compound having at least 1 quaternized nitrogen atom in the ring and may also contain 1 non-adjacent atom of oxygen or sulfur within the ring. Typically, $R_1$–$R_4$ are hydrocarbyl groups of from 1 to about 16 carbon atoms each, with a combined minimum total of about 10 carbon atoms. Preferred ammonium salts have from about 10 to about 30 carbon atoms. A similar formula can be drawn for the phosphonium salts.

The neutralizing anion portion of the salt, i.e. $A^-$ in the above generic formula, may be varied to convenience. Chloride and bromide are the preferred anions, but other representative anions include fluoride, iodide, tosylate, acetate, bisulfate, etc. The following compounds serve as a further illustration: tetraalkylammonium salts, such as tetra-n-butyl-, tri-n-butylmethyl-, tetrahexyl-, trioctylmethyl-, hexadecyltriethyl-, and tridecylmethyl-ammonium chlorides, bromides, iodides, bisulfates, tosylates, etc; aralkylammonium salts, such as tetrabenzyl-, benzyltrimethyl-, benzyltriethyl-, benzyltributyl-, and phenethyltrimethylammonium chlorides, bromides, iodides, etc; arylammonium salts, such as triphenylmethylammonium fluoride, chloride or bromide, N,N,N-trimethylanilinium chloride, N,N,N-triethylanilinium bromide, N,N-diethylanilinium bisulfate, trimethylnaphthyl ammonium chloridde, p-methylphenyltrimethylammonium chloride or tosylate, etc; 5- and 6-membered heterocyclic compounds containing at least 1 quaternary nitrogen atom in the ring, such as N,N-dibutylmorpholinium chloride, N-decylthiazolium chloride, etc, and the corresponding phosphonium salts.

Although stoichiometric amounts of oxidizable organic compound and hypohalite ion are necessary, preferably an excess of hypohalite ion is employed to promote a quantitative reaction. Of course, the particular ratio of organic compound to hypohalite ion will vary with the particular reagents. For example, amines are oxidized in best yields when at least a 2-fold excess of hypohalite ion is used. For amide oxidization, at least a 4-fold excess of hypohalite ion is desirable. The determination of the proper ratio of reagents is well within the skill of the ordinary artisan.

A catalytic amount of the onium salt is required in the practice of this invention. Again, the concentration will vary with particular reagents employed. However, best results are generally achieved when the onium salt concentration is from about 1 mole percent to about 30 mole percent based pon the organic compound to be oxidized. Concentrations between about 2 mole percent and about 10 mole percent are preferred.

Temperature and pressure are not critical to this invention as long as the biphasic mixture remains a liquid. Best results are obtained when the reaction temperatures range from about 0° to about 35° C with ambient temperature and pressure preferred.

Although the reaction can be conducted neat, it is preferably conducted in the presence of an inert, water-immiscible organic solvent. Typical solvents include benzene, chlorobenzene, o-dichlorobenzene, hexane, methylene chloride, chloroform, carbon tetrachloride, and the like. Not only do these solvents contribute to the formation of a biphasic reaction mixture, but they also aid in moderating reaction rate and temperature.

Generally, at least sufficient solvent to dissolve the oxidizable organic compound is used and preferably the amount of solvent used is equal in volume to the amount of aqueous hypohalite used. Practical considerations of reaction vessel size, product recovery, etc. are the only limitations upon the maximum amount of solvent that can be used.

The following examples are illustrative embodiments of this invention.

EXAMPLE 2 p-Methylbenzyl alcohol (1.2515 g, 0.0103 mole) 2-chloronaphthalene (0.8747 g, used as an internal standard for gas chromatography), and tetra-n-butylammonium bisulfate (0.1841 g, 0.0005 mole) were dissolved in 25 ml of methylene chloride. To this solution was added 25 ml of 12 percent aqueous sodium hypochlorite (2.95 g, 0.04 mole). The biphasic mixture was stirred under ambient conditions (24° C, atmospheric pressure) and monitored periodically by gas chromatography. After 1.9 hours reaction time, 85.2 percent of the p-methylbenzyl alcohol had been converted to p-tolualdehyde.

EXAMPLE 3

A mixture of α-phenylacetamide (1.3535 g, 0.01 mole), nitrobenzene (1.034 g, employed as an internal standard for gas phase chromatography) and tetra-n-butylammonium bisulfate (0.125 g, 0.00037 mole) in 25 ml of methylene chloride was stirred under ambient conditions (23° C, atmospheric pressure) with 50 ml of 12 percent aqueous sodium hypochlorite (5.85 g, 0.079 mole). After 2.5 hours reaction time, the organic phase was analyzed by vapor phase chromatography and was found to contain 62 percent benzonitrile.

EXAMPLES 4–11

Under conditions similar to Example 1, various other organic compounds were oxidized. The particular reagents and results are tabulated in Table I.

TABLE I

| Ex | Organic Compound (Mole) | Quaternary Onium Salt (Mole) | Alkali Metal Hypohalite (Mole) | Solvent | Reaction (minutes) | Product (%) |
|---|---|---|---|---|---|---|
| 4 | p-Nitrobenzyl Alcohol (0.086) | Bu$_4$NCl[1] (0.008) | KOCl (0.04) | CH$_2$Cl$_2$ | 65 | p-Nitrobenzaldehyde (83) |
| 5 | o-Methoxybenzyl Alcohol (0.4) | Bu$_4$NHSO$_4$[2] (0.02) | NaOCl (0.04) | CH$_2$Cl$_2$ | 316 | o-Methoxybenzaldehyde (84) |
| 6 | p-Chlorobenzyl Alcohol (0.4) | Bu$_4$NHSO$_4$ (0.02) | NaOCl (0.04) | CH$_2$Cl$_2$ | 335 | p-Chlorobenzaldehyde (98) |
| 7 | 9-Fluorenol (0.4) | Bu$_4$NHSO$_4$ (0.02) | NaOCl (0.04) | CH$_2$Cl$_2$ | 51 | 9-Fluorenone (93) |
| 8 | Benzhydrol (0.4) | Bu$_4$NHSO$_4$ (0.02) | NaOCl (0.04) | CH$_2$Cl$_2$ | 345 | Benzophenone (95) |
| 9 | Norbornyl ammonium chloride (0.01) | Bu$_4$NCl (0.0002) | NaOCl (0.08) | CHCl$_3$ | 90 | Norbornanone (70) |
| 10 | Cyclohexylamine (0.01) | Bu$_4$NCl (0.0002) | NaOCl (0.08) | CH$_2$Cl$_2$ | 120 | Cyclohexanone (38) 2-chlorocyclohexanone (55) |
| 11 | n-Octyl Amine (0.01) | Bu$_4$NCl (0.0005) | NaOCl (0.08) | CH$_2$Cl$_2$ | 95 | Octanoyl Nitrile (57) |

Footnotes:
[1]Tetra-n-butylammonium chloride
[2]Tetra-n-butylammonium bisulfate

EXAMPLE 1

A solution of benzyl alcohol (1 g, 0.0093 mole), naphthalene (1.02 g, used as an internal standard for gas chromatography), and tetra-n-butylammonium chloride (0.122 g, 0.00044 mole) in 40 ml of methylene chloride, was stirred at approximately 23° C with 40 ml of 12 percent aqueous sodium hypochlorite solution (4.96 g, 0.067 mole). The reaction mixture was occasionally cooled by an external water bath to keep the reaction temperature from exceeding 30° C. The reaction was monitored by gas chromatography. At 6.8 hours reaction time, 97 percent of the benzyl alcohol had been converted to benzaldehyde.

What is claimed is:
1. A process for oxidizing an organic compound selected from the group consisting of amines, amides, alkanals, primary and secondary alkanols, and organic compounds containing an activated double bond with aqueous hypohalite ion comprising reacting by contacting:
   a. a water-immiscible, liquid organic phase comprising the organic compound; with
   b. an aqueous phase containing hypohalite ion; and
   c. a catalytic amount of a quaternary ammonium salt and/or a quaternary phosphonium salt.
2. The process of claim 1 wherein the hypohalite ion is hypochlorite.

3. The process of claim 2 wherein the quaternary ammonium and phosphonium salts are of the formula $R_1R_2R_3R_4Q^+A^-$, wherein $Q^+$ is a quaternized nitrogen or phosphorus atom, $A^-$ is a neutralizing anion, and $R_1$–$R_4$ are individually hydrocarbyl groups of from 1 to about 16 carbon atoms each, with a combined minimum total of about 10 carbon atoms.

4. The process of claim 3 wherein the quaternary ammonium and phosphonium salts have from about 10 to about 30 carbon atoms.

5. The process of claim 2 wherein the quaternary ammonium salt is tetra-n-butylammonium-, benzyltriethylammonium-, or benzyltrimethylammonium chloride or bisulfate.

6. The process of claim 5 wherein the reaction is conducted at a temperature of from about 0° to about 35° C.

7. The process of claim 6 wherein the water-immiscible, liquid organic phase comprises the organic compound and and inert, water-immiscible organic solvent.

8. The process of claim 1 wherein the organic compound is a primary or secondary alkanol.

9. The process of claim 1 wherein the organic compound is 9-fluorenol, benzhydrol, or benzyl, p-methylbenzyl, p-nitrobenzyl, o-methoxybenzyl or p-chlorobenzyl alcohol.

10. The process of claim 1 wherein the organic compound is an amine or amide.

11. The process of claim 1 wherein the organic compound is α-phenylacetamide, cyclohexylamine, n-octyl amine or norbornyl ammonium chloride.

12. The process of claim 1 wherein the organic compound is an alkanal.

13. The process of claim 1 wherein the organic compound contains an activated double bond.

* * * * *